(12) United States Patent
Li

(10) Patent No.: US 10,278,658 B2
(45) Date of Patent: May 7, 2019

(54) RADIATION RESIDUE SCANNING DEVICE AND SYSTEM

(71) Applicant: Beijing Explore Times Technology Co., Ltd., Beijing (CN)

(72) Inventor: Gaofeng Li, Beijing (CN)

(73) Assignee: Beijing Explore Times Technology Co., Ltd., Beijing (CN)

(*) Notice: Subject to any disclaimer, the term of this patent is extended or adjusted under 35 U.S.C. 154(b) by 0 days.

(21) Appl. No.: 15/892,370

(22) Filed: Feb. 8, 2018

(65) Prior Publication Data

US 2018/0228453 A1   Aug. 16, 2018

(30) Foreign Application Priority Data

Feb. 10, 2017  (CN) .......................... 2017 1 0075957

(51) Int. Cl.
*A61B 6/00*   (2006.01)

(52) U.S. Cl.
CPC .......... *A61B 6/4258* (2013.01); *A61B 6/4266* (2013.01); *A61B 6/4476* (2013.01); *A61B 6/461* (2013.01); *A61B 6/54* (2013.01); *A61B 6/545* (2013.01)

(58) Field of Classification Search
CPC ............................. A61B 6/4258; A61B 6/4266
See application file for complete search history.

(56) References Cited

U.S. PATENT DOCUMENTS

| 2004/0129887 A1* | 7/2004 | Vydrin | G01T 1/1644 250/367 |
| 2011/0036989 A1* | 2/2011 | Marks | G01T 1/17 250/370.08 |
| 2011/0152679 A1* | 6/2011 | Morag | A61B 6/037 600/431 |
| 2012/0085942 A1* | 4/2012 | Birman | G21K 1/025 250/505.1 |
| 2013/0010921 A1* | 1/2013 | Sagoh | A61B 6/032 378/19 |
| 2013/0284940 A1* | 10/2013 | Herrmann | G01T 1/17 250/393 |
| 2015/0057526 A1* | 2/2015 | Gerken | A61B 6/54 600/411 |

* cited by examiner

*Primary Examiner* — Yara B Green
(74) *Attorney, Agent, or Firm* — Marshall, Gerstein & Borun LLP

(57) ABSTRACT

A radiation residue scanning device includes a plurality of CZT detectors, a plurality of data processing units, a plurality of window acquisition circuits, a plurality of counting units, and a processor; the plurality of CZT detectors connected in one-to-one correspondence to the plurality of data processing units; the plurality of data processing units are connected in one-to-one correspondence to the plurality of window acquisition circuits; and the plurality of window acquisition circuits are connected in one-to-one correspondence to the counting units The window acquisition circuit includes a plurality of acquisition modules, and the respective acquisition modules are connected in parallel; the counting unit includes a plurality of counting subunits, the counting subunits are connected in one-to-one correspondence to the acquisition window modules, and the processor is connected to the plurality of counting units.

16 Claims, 3 Drawing Sheets

RADIATION RESIDUE SCANNING DEVICE AND SYSTEM

CROSS-REFERENCE TO RELATED APPLICATION

The present application claims priority to Chinese Patent Application No. 201710075957.6, filed Feb. 10, 2017. The priority application, CN 201710075957.6, is hereby incorporated by reference.

TECHNICAL FIELD

The present disclosure relates to the technical field of nuclear medicine imaging, and in particular to a radiation (radioactive material) residue scanning device and system.

BACKGROUND ART

At present, high-energy elements, for example iodine-131 element, are more and more widely used in nuclear medicine, and especially application of iodine-131 to thyroid diseases, such as diagnostic iodine-131 systemic imaging, post-treatment iodine-131 systemic imaging, removal of residual thyroid tissue after thyroid cancer surgery and treatment of recurrence and metastatic tissue with iodine-131, etc., has a significant effect in treatment with safety and convenience, and is thus a radionuclide therapy project developing most rapidly in China.

A patient treated with iodine-131 needs to be monitored for radiation dose residues for better observation and analysis of the disease condition. At present, an distribution image of iodine-131 in a human body is obtained by γ-ray imaging technology in nuclear medicine. Once iodine-131 nuclide decays in the human body, γ particles are released in random directions. After the γ particles directly facing a detector pass through the human body, they will be captured by a crystal and release a certain number of photons. A photoelectric sensor converts the photons into electrons and outputs the same in the form of current pulses to a preamplifier circuit. The current signal is converted by an integration circuit into a voltage signal. Here, the capability of the γ particles is linearly correlated with the number of the photons and the amplitude of the voltage signal. Through the above process, a counter (an arithmometer) is added on a corresponding position of the image picture. With an increase of the duration of the acquisition, the count at different positions of the image increase constantly. The magnitude of the counted values at each position is linearly correlated with the amount of iodine-131 at a corresponding position of the human body. In this manner, the counted values are converted to a grayscale image, which is the distribution image of iodine-131 in the human body.

Specifically, the γ particles released from iodine-131 mainly contain particles of two energy levels: 284 keV and 365 keV, while the proportions of particles of other two branches of energy levels (80 keV and 723 keV) are very small (negligible in an actual acquisition process). In an actual detection process, after the γ particles of the same energy are acquired, a normally distributed sharp peak is formed. The ratio of the width at half peak value to the peak value is the so-called energy resolution in nuclear physics. In general, the narrower is the energy peak value, the smaller is the energy resolution value, and the better is the energy resolution performance.

Iodine-131 releases γ particles in random directions, and the released γ particles will be subjected to Compton scattering after colliding with an object. In an energy spectrogram of the γ particles released from iodine-131, the left side of the full energy peak is a Compton plateau that is generated from the Compton scattering effect. The γ-rays generated from the scattered γ particles are not what we need and need to be filtered in the subsequent circuit part by a window setting. Otherwise the finally generated iodine-131 distribution image would be blurred, and the spatial resolution of the image would be affected. In order to improve the acquisition efficiency and thus acquire all the γ-rays of various energy levels, it is necessary to adequately increase the width of the window in the circuit. Moreover, considering that the number of γ-rays at a low energy level of 284 KeV is small and their contribution in the energy spectrum falls within the Compton plateau, it is thus difficult to distinguish the energy peak of the γ-rays at 284 KeV from the Compton plateau. Thus, by increasing the width of the window, the number of the scattered ineffective γ-rays which are marked as effective γ-rays also increased therealong, which ultimately affects the spatial resolution of the image. In view of the above, the prior residue scanning device still has the problems of low detection efficiency and poor spatial resolution.

DISCLOSURE OF THE INVENTION

In view of the above, the object of embodiments of the present disclosure is to provide a radiation residue scanning device and system, in which a modification is made to subsequent circuits according to a CZT (Cadmium Zinc Telluride) detector, the modification referring to reducing the width of a acquisition window while increasing the number of the acquisition windows. The provided radiation residue scanning device and system solve the problems of low detection efficiency and poor spatial resolution, increase the detection efficiency of the detector, and improve the spatial resolution of the image.

In a first aspect, an embodiment of the present disclosure provides a radiation residue scanning device; the device includes a plurality of CZT detectors, a plurality of data processing units, a plurality of window acquisition circuits, a plurality of counting units, and a processor;

wherein the plurality of CZT detectors are connected in one-to-one correspondence to the plurality of data processing units; the plurality of data processing units are connected in one-to-one correspondence to the plurality of window acquisition circuits; and the plurality of window acquisition circuits are connected in one-to-one correspondence to the plurality of counting units;

the CZT detector captures a γ-ray emitted from a body of a patient; a photon is released from the γ-ray to excite an electron by a photoelectric effect or a Compton effect, so as to form a current signal; and the current signal is sent to the data processing unit;

the data processing unit receives the current signal, converts the current signal into a voltage pulse signal, and sends the voltage pulse signal to the window acquisition circuit;

the window acquisition circuit receives the voltage pulse signal, performs window acquisition of the voltage pulse signal to generate a counting pulse signal, and sends the counting pulse signal to the counting unit, wherein the window acquisition circuit includes a plurality of acquisition modules, and the respective acquisition modules are connected in parallel and configured to acquire the voltage pulse signals of different amplitudes;

the counting unit includes a plurality of counting subunits, the counting subunits are connected in one-to-one correspondence to the acquisition modules; the counting subunit receives the counting pulse signal, counts the counting pulse signal to obtain a counted value, and sends the counted value to the processor; and the processor is connected to each of the counting subunits, and the processor receives the counted values and generates an in vivo radioactive material distribution grayscale image based on the counted values.

In combination with the first aspect, the embodiment of the present disclosure provides a first possible embodiment of the first aspect, wherein the plurality of CZT detectors are arranged in a form of linear array.

In combination with the first aspect, the embodiment of the present disclosure provides a second possible embodiment of the first aspect, wherein each of the data processing units includes an amplifier and an integrator; the CZT detector, the amplifier, the integrator, and the window acquisition circuit are connected in sequence.

In combination with the first aspect, the embodiment of the present disclosure provides a third possible embodiment of the first aspect, wherein the acquisition module includes a high threshold voltage comparator and a low threshold voltage comparator that are connected in parallel; and the counting subunit includes two counters (arithmometers), and the high threshold voltage comparator and the low threshold voltage comparator are connected in one-to-one correspondence to the two counters.

In combination with the second possible implementation of the first aspect, the embodiment of the present disclosure provides a fourth possible embodiment of the first aspect, wherein the data processing unit further includes a pulse shaping circuit, an input terminal of the pulse shaping circuit is connected to an output terminal of the integrator, and an output terminal of the pulse shaping circuit is connected to an input terminal of the window acquisition circuit.

In combination with the first aspect, the embodiment of the present disclosure provides a fifth possible embodiment of the first aspect, wherein the device further includes a collimator; the collimator is provided with a plurality of channels, the respective channels are connected in one-to-one correspondence to the respective CZT detectors, and the channel captures the γ-ray such that the γ-ray is transmitted to the CZT detector.

In combination with the first aspect, the embodiment of the present disclosure provides a sixth possible embodiment of the first aspect, wherein the device further includes a display which is connected to the processor and configured to receive and display the in vivo radioactive material distribution grayscale image.

In combination with the third possible embodiment of the first aspect, the embodiment of the present disclosure provides a seventh possible embodiment of the first aspect, wherein the device further includes a latch which is connected to the counter and the processor; and the counted value sent from the counter are latched in the latch, and the counted value is transmitted by the latch to the processor for processing.

In a second aspect, an embodiment of the present disclosure also provides a radiation residue scanning system, including: a base, a support body, a height measuring device, a lifting device, and the radiation residue scanning device as described in any one of the embodiments of the first aspect;

wherein the base is connected to the support body and configured to accommodate a patient in a standing state, and the height measuring device is mounted to the support body and configured to measure a height of the patient;

the height measuring device is connected to the processor, and the processor is further configured to receive the height, determine an initial scanning position and a final scanning position based on the height, and send a driving signal to the lifting device; and the lifting device is mounted, movably up and down, to the support body, and the radiation residue scanning device is mounted in the lifting device;

the lifting device is electrically connected to the processor; and the lifting device is configured to bring the radiation residue scanning device to move up and down based on the driving signal.

In combination with the second aspect, the embodiment of the present disclosure provides a first possible embodiment of the second aspect, wherein the system further includes a speed sensor electrically connected to the processor; the speed sensor is mounted to the lifting device; and the speed sensor is configured to acquire a moving speed of the lifting device and send the moving speed to the processor.

The embodiments of the present disclosure bring about the following beneficial effects: The radiation residue scanning device provided by the embodiments of the present disclosure includes a plurality of CZT detectors, a plurality of data processing units, a plurality of window acquisition circuits, a plurality of counting units, and a processor; the plurality of CZT detectors are connected in one-to-one correspondence to the plurality of data processing units; the plurality of data processing units are connected in one-to-one correspondence to the plurality of window acquisition circuits; the plurality of window acquisition circuits are connected in one-to-one correspondence to the counting units; wherein the window acquisition circuit includes a plurality of acquisition modules, and the respective acquisition modules are connected in parallel; the counting unit includes a plurality of counting subunits; the counting subunits are connected in one-to-one correspondence to the acquisition modules, and the processor is connected in one-to-one correspondence to the plurality of counting subunits. In the embodiments of the present disclosure, the current signal acquired by the CZT detector is processed by the data processing unit to generate a voltage pulse signal, then the voltage pulse signal is acquired by each of the acquisition modules in the window acquisition circuit and the voltage pulse signal is separated into counting pulse signals of different amplitudes, and the respective counting pulse signals are counted by the counting subunits to obtain a plurality of counted values, and finally an in vivo radioactive material distribution grayscale image is generated based on the respective counted values. Here, the size of the acquisition window in the acquisition module is set based on the energy resolution of the CZT detector. Thus, since the CZT detector has a better energy resolution, it is possible to provide relatively narrow acquisition windows while increasing the number of the acquisition windows, so as to the problems of low detection efficiency and poor spatial resolution, and to increase the detection efficiency of the detector, and improve the spatial resolution of the image.

Other features and advantages of the present disclosure will be set forth in the description below, and in part will become apparent from the description, or may be learned by a practice of the present disclosure. The objectives and other advantages of the present disclosure will be achieved and attained by the structure particularly pointed out in the description and claims as well as the appended drawings.

In order to make the above objects, features and advantages of the present disclosure more apparent and comprehensible, preferred embodiments will be given hereinafter and described in detail below with reference to the accompanying drawings.

BRIEF DESCRIPTION OF DRAWINGS

For illustrating technical solutions in specific embodiments of the present disclosure or in the prior art more clearly, drawings used in the description of the specific embodiments or of the prior art will be introduced briefly below. It is apparent that the drawings in the following description are illustrative of part of the embodiments of the present disclosure, and it would be understood by those skilled in the art that other drawings could also be obtained from these drawings without making any inventive effort.

REFERENCE NUMERALS

100—CZT detector; 200—data processing unit; 210—amplifier; 220—integrator; 230—pulse shaping circuit; 300—window acquisition circuit; 400—counting unit; 500—processor; 51—base; 52—supporting body; 53—top plate; 54—lifting device; 55—radiation residue scanning device.

DETAILED DESCRIPTION OF EMBODIMENTS

In order to make the objects, technical solutions and advantages of the embodiments of the present disclosure more clear, the technical solutions of the present disclosure will be described below clearly and completely with reference to the drawings. It is apparent that the embodiments to be described are part, but not all, of the embodiments of the present disclosure. All the other embodiments obtained by those skilled in the art in light of the embodiments of the present disclosure without making inventive efforts would fall within the scope of the present disclosure as claimed.

At present, the prior residue scanning device still has problems of low detection efficiency and poor spatial resolution. In view of such, in a radiation residue scanning device and system provided in embodiments of the present disclosure, a modification is made to follow-up circuit with respect to a CZT detector. The modification is directed to reducing the width of an acquisition window while increasing the number of the acquisition windows, thereby solving the problems of low detection efficiency and poor spatial resolution, increasing the detection efficiency of the detector, and improving the spatial resolution of the image.

To facilitate the understanding of this embodiment, a radiation residue scanning device disclosed in an embodiment of the present disclosure will be illustrated in detail.

First Embodiment

Figure 1:
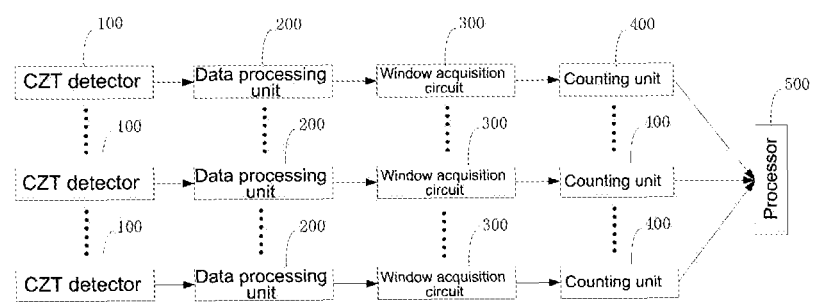
FIG. 1 is a schematic diagram of the structure of a radiation residue scanning device provided in an embodiment of the present disclosure.

FIG. 1 is a schematic diagram of the structure of a radiation residue scanning device provided in an embodiment of the present disclosure, and as shown in FIG. 1, the device includes a plurality of CZT (cadmium zinc telluride, CdZnTe) detectors 100, a plurality of data processing units 200, a plurality of window acquisition circuits 300, a plurality of counting units 400, and a processor 500. Specifically, the plurality of CZT detectors 100 are connected in one-to-one correspondence to the plurality of data processing units 200; the plurality of data processing units 200 are connected in one-to-one correspondence to the plurality of window acquisition circuits 300; and the plurality of window acquisition circuits 300 are connected in one-to-one correspondence to the plurality of counting units 400.

The CZT detector 100 captures γ-rays emitted from a patient's body. The γ-rays release photons and excite electrons by photoelectric effect or Compton effect to form a current signal, and the current signal is sent to the data processing unit 200. Specifically, after the patient is treated with iodine-131, iodine-131 releases γ-rays in all directions in the patient's body, the γ-rays pass through substances and interact with atoms to release γ photons, and then the γ photons undergo a photoelectric effect to transfer all the energy to the bound electrons, such that the electrons are unbound from the atoms and emitted out, and the photons themselves disappear; or alternatively, the γ photons undergo the Compton effect to collide with free static electrons, such that the electrons turn into recoil electrons, and that the γ photons are scattered and the original energy and direction are changed. The excited free electrons above form a current signal which is transmitted to the data processing unit 200. Preferably, for the convenience of subsequent processing, the plurality of CZT detectors 100 are arranged in a form of linear array.

After receiving the current signal, the data processing unit 200 converts the current signal into a voltage pulse signal and sends the voltage pulse signal to the window acquisition circuit 300.

Figure 2:
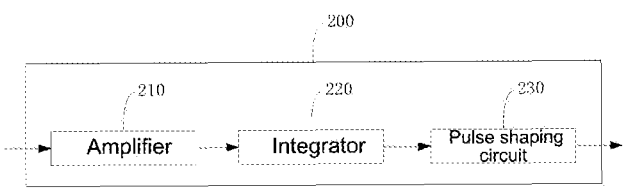
FIG. 2 is a schematic diagram of the structure of a data processing unit in the radiation residue scanning device provided in the embodiment of the present disclosure.

Preferably, as shown in FIG. 2, each of the data processing units 200 includes an amplifier 210 and an integrator 220. The CZT detector 100, the amplifier 210, the integrator 220, and the window acquisition circuit 300 are connected in sequence. The current signal is firstly amplified by the amplifier 210 to generate a current amplified signal, and the amplifier 210 sends the current amplified signal to the integrator 220. The integrator 220 integrates the current amplified signal to generate a voltage pulse signal, and then the voltage pulse signal is sent to the window acquisition circuit 300.

Further, in order to facilitate accurate acquisition of the voltage pulse signal by the follow-up window acquisition circuit 300, in one example, the data processing unit 200 further includes a pulse shaping circuit 230. An input terminal of the pulse shaping circuit 230 is connected to an output terminal of the integrator 220, and an output terminal of the pulse shaping circuit 230 is connected to an input terminal of the window acquisition circuit 300.

Figure 3:
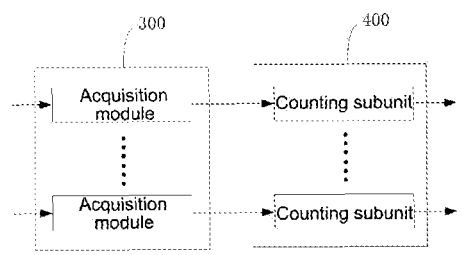
FIG. 3 is a schematic diagram of the connection between a window acquisition circuit and a counting unit in the radiation residue scanning device provided in the embodiment of the present disclosure.

The window acquisition circuit 300 receives the voltage pulse signal, performs a window acquisition of the voltage pulse signal to generate a counting pulse signal, and sends the counting pulse signal to the counting unit 400. Considering that iodine-131 contains γ-rays at various energy levels, in order to count effective γ-rays at different energy levels as more as possible, the window acquisition circuit 300 includes a plurality of acquisition modules as shown in FIG. 3, and the respective acquisition modules are connected in parallel for collecting voltage pulse signals of different amplitudes, such that γ-rays corresponding to different energy levels (such as γ-rays at energy levels of 365 KeV and 284 KeV) can be separated and acquired. As a result, the detection efficiency of the CZT detector 100 is improved.

Specifically, the width of an acquisition window in each of the acquisition modules can be adjusted based on the energy resolution of the CZT detector 100. Since the CZT detector 100 has a good energy resolution, an energy peak with a narrow width can be obtained. Therefore, each of the acquisition modules can be designed to have a relatively narrow acquisition window so as to acquire most γ-rays that are effective, while reduce the acquisition of ineffective γ-rays (such as the scattered γ-rays), and reduce the influence of the ineffective γ-rays on the spatial resolution of the image. For example, after γ-rays at 284 KeV falling within the Compton plateau pass through the relatively narrowly provided acquisition window, in the embodiment of the present disclosure, most of effective γ-rays at 284 KeV can be acquired while ineffective γ-rays have been filtered as many as possible. As a result, the spatial resolution of the image is improved.

Further, the counting unit 400 includes a plurality of counting subunits, the counting subunits are connected in one-to-one correspondence to the acquisition modules. The counting subunit receives the counting pulse signal, counts the counting pulse signal to obtain a counted value, and sends the counted value to the processor 500.

Preferably, in one embodiment, the acquisition module includes a high threshold voltage comparator and a low threshold voltage comparator connected in parallel, the counting subunit includes two counters, and the high threshold voltage comparator and the low threshold voltage comparator are connected in one-to-one correspondence to the two counters.

Figure 4:
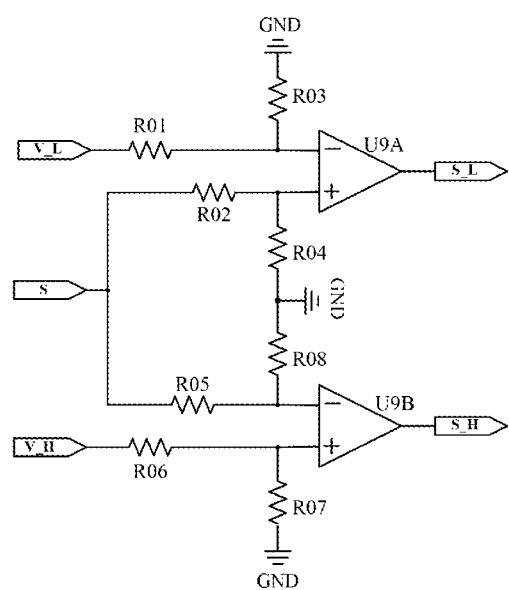
FIG. 4 is a circuit connection diagram of an acquisition module in the radiation residue scanning device provided in the embodiment of the present disclosure.

FIG. 4 shows a circuit connection diagram of the acquisition module in the radiation residue scanning device provided in the embodiment of the present disclosure. As shown in FIG. 4, each voltage pulse signal S is sent to inverting input terminals of the low threshold voltage comparator U9A and of the high threshold voltage comparator U9B, respectively. Moreover, two voltage signals which are a low threshold voltage V_L and a high threshold voltage V_H are inputted to non-inverting input terminals of the low threshold voltage comparator U9A and of the high threshold voltage comparator U9B. Assuming that the low threshold voltage V_L and the high threshold voltage V_H are 3V and 5V, respectively, the low threshold voltage comparator U9A outputs a high level when the voltage pulse signal S is higher than the low threshold voltage 3V, and otherwise it outputs a low level; and the high threshold voltage comparator U9B outputs a high level when the voltage pulse signal S is higher than the high threshold voltage 5V, and otherwise it outputs a low level. Accordingly, the high and low levels output by the low threshold voltage comparator U9A and the high threshold voltage comparator U9B form two different counting pulse signals S_L, S_H, respectively. The counters connected to the low threshold voltage comparator U9A and to the high threshold voltage comparator U9B count the two counting pulse signals S_L and S_H, respectively, to obtain two counted values. The difference between the two counted values is the count of the "window(s)" between the high and low thresholds 5V and 3V. Here, the voltage signal above can be outputted by a DAC chip.

The processor 500 is connected to each of the counting subunits, and the processor 500 receives the counted values sent from the respective counters in the respective counting subunits, and generates an in vivo radioactive material distribution grayscale image (a grayscale image of the distribution of radioactive material in the body) based on the counted values.

In the above embodiment, the device further includes a collimator, the collimator is provided with a plurality of channels, and the respective channels are connected in one-to-one correspondence to the respective CZT detectors 100 for capturing γ-rays, such that the γ-rays are transmitted to the CZT detectors 100. Specifically, the plurality of channels can all receive the γ-rays emitted from any part of the patient. Each channel receives only rays that are parallel to the collimator, and does not receive rays that form an oblique angle with respect to the collimator. Namely, the collimator functions to collimate the rays. Preferably, the collimator is a collimator that can be applicable to high-energy elements.

Further, the above device further includes a display which is connected to the processor 500 for receiving and displaying the in vivo radioactive material distribution grayscale image sent from the processor 500, such that the distribution of the radioactive material in the body can be visually observed.

In one embodiment, in consideration of a problem of non-synchronous data exchange speeds between the processor 500 and the counter, the device further includes a latch which is connected to the counter and the processor 500. The counted values sent from the counter are latched by the latch and transmitted by the latch to the processor 500 for processing. Specifically, the processor 500 includes a storage unit, a reading unit, and a calculation unit. The latch latches the counted value under the control of a control signal and sends the counted value to the storage unit of the processor 500, and the reading unit of the processor 500 reads the counted value from the storage unit and transmits the counted value to the calculation unit of the processor 500 for analysis and calculation.

The radiation residue scanning device provided by the present disclosure includes a plurality of CZT detectors 100, a plurality of data processing units 200, a plurality of window acquisition circuits 300, a plurality of counting units 400, and a processor 500; the plurality of CZT detectors 100 are connected in one-to-one correspondence to the plurality of data processing units 200; the plurality of data processing units 200 are connected in one-to-one correspondence to the plurality of window acquisition circuits 300; the plurality of window acquisition circuits 300 are connected in one-to-one correspondence to the counting units 400; here, the window acquisition circuit 300 includes a plurality of the acquisition modules, and the respective acquisition modules are connected in parallel; the counting unit 400 includes a plurality of counting subunits, and the counting subunits are connected in one-to-one correspondence to the acquisition modules; and the processor 500 is connected in one-to-one correspondence to the plurality of counting subunits. In the embodiment of the present disclosure, the current signal acquired by the CZT detector 100 is processed by the data processing unit 200 to generate a voltage pulse signal; then the voltage pulse signal is acquired by each of the acquisition modules in the window acquisition circuit 300 and the voltage pulse signal is separated into counting pulse signals of different amplitudes, and the respective counting pulse signals are counted by the counting subunits to obtain a plurality of counted values; and finally an in vivo radioactive material distribution grayscale image is generated by the processor 500 based on the respective counted values. Here, the size of the acquisition window in the acquisition module is set based on the energy resolution of the CZT detector 100. Thus, since the CZT detector 100 has a better energy resolution, it is possible to set relatively narrow acquisition windows while increasing the number of the acquisition windows, so as to solve the problems of low detection efficiency and poor spatial resolution, and to increase the detection efficiency of the detector, and improve the spatial resolution of the image.

Second Embodiment

Figure 5:
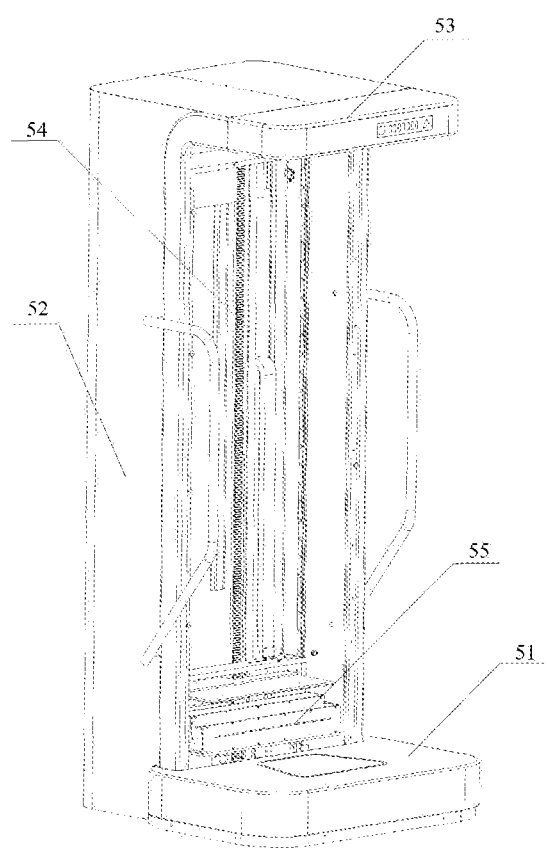
FIG. 5 is a schematic diagram of the structure of a radiation residue scanning system provided in an embodiment of the present disclosure.

FIG. 5 shows a schematic diagram of the structure of a radiation residue scanning system provided in an embodiment of the present disclosure. As shown in FIG. 5, the system includes a base 51, a support body, a height measuring device, a lifting device 54, and a radiation residue scanning device 55 as in First Embodiment.

Here, the base 51 is connected to the support body for bearing a patient in a standing state. The height measuring device is mounted to the support body for measuring the height of the patient. The height measuring device is connected to the processor 500, and the processor 500 receives the above height and determines an initial scanning position and a final scanning position based on the height, and send a driving signal to the lifting device 54.

Specifically, the radiation residue scanning device 55 can be mounted in the lifting device 54, and the lifting device 54 can be mounted, movably up and down, to the support body, and electrically connected to the processor 500 for setting the radiation residue scanning device 55 to move up and down based on the above driving signal.

Further, as shown in FIG. 5, the support body may include a supporting body 52 and a top plate 53. Here, a first end (lower end in FIG. 5) of the supporting body 52 is connected to the base 51, a second end (upper end in FIG. 5) of the supporting body 52 is connected to the top plate 53, and the top plate 53 is arranged opposite to the base 51. Specifically, the supporting body 52 is sandwiched between the top plate 53 and the base 51. The supporting body 52 has a preset height which can be determined according to the actual situation, but should enable each of patients of different heights to stand between the base 51 and the top plate 53. A hollow cavity may be provided inside the supporting body 52, and the lifting device 54 and the radiation residue scanning device 55 are both mounted in the hollow cavity.

In the actual case, a patient stands on the base 51 and remains in a stationary state. The height measuring device measures the height of the patient, and sends the measured height to the processor 500. The processor 500 receives the height, determines an initial scanning position and a final scanning position based on the height, and sends a driving signal. The lifting device 54 receives the driving signal sent from the processor 500, and moves from the initial scanning position to the final scanning position based on the driving signal. Since the radiation residue scanning device 55 is mounted on the lifting device 54, the movement of the lifting device 54 drives the radiation residue scanning device 55 to move from the initial scanning position to the final scanning position. The radiation residue scanning device 55 scans the body of the patient that corresponds to all the positions between the initial scanning position and the final scanning position in real time during the movement from the initial scanning position to the final scanning position along with the lifting device 54, and converts the received γ-rays into counted values by processing and analysis, and sends the counted values as a scanning result to the processor 500. The processor 500 receives the scanning result and generates an in vivo radioactive material distribution grayscale image based on the scanning result. Upon completion of the scanning, the patient may leave the base 51.

Specifically, the number of CZT detectors 100 constituting the linear array in the radiation residue scanning device 55 and the scanning speed may be determined based on the image pixels required by the user. For example, if the pixels of the image are 100*800, 100 CZT detectors 100 may be provided to constitute an array. The radiation residue scanning device 55 is activated, and the radiation residue scanning device 55 is driven by the lifting device 54 to move once every predetermined time at a certain speed from the initial scanning position until it moves 800 times to the final scanning position to complete the whole scanning process. Thus, the processor 500 processes each scanning result and maps the same to a corresponding pixel point of the image, so as to generate a corresponding in vivo grayscale image of the distribution of radiation residues.

Further, in order to be in better control of the moving speed of the radiation residue scanning device 55, the system further includes a speed sensor electrically connected to the processor 500. The speed sensor is mounted to the lifting device 54 for acquiring a moving speed of the lifting device 54 and sending the moving speed to the processor 500. The processor 500 sends a speed adjustment command to the lifting device 54 based on the moving speed, and the movement of the lifting device 54 follows a certain speed based on the speed adjustment command. In this way, the processor 500 achieves an automatic control of the lifting device 54.

The radiation residue scanning system provided in the embodiment of the present disclosure has the same technical features as the radiation residue scanning device provided in the above embodiment, and therefore can also solve the same technical problem and achieve the same technical effect.

It will be clearly understood by those skilled in the art that for the convenience and simplicity of the description, the specific working process of the radiation residue scanning device and system described above can be performed with reference to the corresponding process in the foregoing embodiment of method and will not be described in detail herein.

In addition, in the description of the embodiment of the present disclosure, unless otherwise expressly specified or defined, terms of "mounted", "coupled", and "connected" should be understood broadly. For example, connection may be fixed connection or detachable connection or integral connection, may be mechanical connection or electric connection, or may be direct coupling or indirect coupling via an intermediate medium or internal communication between two elements. The specific meanings of the above terms in the present disclosure could be understood by those skilled in the art according to specific situations.

In the description of the present disclosure, it should be noted that orientation or positional relations indicated by the terms such as "center", "up", "down", "left", "right", "vertical", "horizontal", "inside", and "outside" are the orientation or positional relations shown in the figures, and these terms are intended only to facilitate the description of the present disclosure and simplify the description, but not intended to indicate or imply that the referred devices or elements must be in a particular orientation or constructed or operated in the particular orientation, and therefore should not be construed as limiting the present disclosure. In addition, terms such as "first", "second", and "third" are used only for the purpose of description, and should not be understood as indicating or implying a relative importance.

Finally, it should be noted that the embodiments described above are merely specific embodiments of the present disclosure for illustrating the technical solutions of the present disclosure, but not intended to limit the invention, and the scope of claims of the present disclosure is not limited thereto. Although the present disclosure has been described in detail with reference to the foregoing embodiments, it should be understood by those skilled in the art that, any person skilled in the art may modify the technical solutions disclosed in the foregoing examples or easily conceive of variations thereof or substitute part of the technical features with equivalents within the scope of the technique disclosed in the present disclosure; and all these modifications, variations or substitutions will not cause the spirit of the corresponding technical solutions to depart from the gist and scope of the technical solutions of the embodiments of the present disclosure and should be encompassed in the scope of claims of the present disclosure. Therefore, the scope of the present disclosure should be determined based on the scope of the claims.

What is claimed is:

1. A radiation residue scanning device, comprising a plurality of CZT (Cadmium Zinc Telluride) detectors, a plurality of data processing units, a plurality of window acquisition circuits, a plurality of counting units, and a processor;
   wherein the plurality of CZT detectors are connected in one-to-one correspondence to the plurality of data processing units; the plurality of data processing units are connected in one-to-one correspondence to the plurality of window acquisition circuits; and the plurality of window acquisition circuits are connected in one-to-one correspondence to the plurality of counting units;
   each of the CZT detectors is configured to capture a γ-ray emitted from a body of a patient, cause a photon to be released to excite, through a photoelectric effect or a Compton effect, an electron so as to form a current signal, and is configured to send the current signal to a corresponding one of the data processing units;
   each of the data processing units is configured to receive the current signal, convert the current signal into a voltage pulse signal, and send the voltage pulse signal to a corresponding one of the window acquisition circuits;
   each of the window acquisition circuits is configured to receive the voltage pulse signal, perform window acquisition on the voltage pulse signal to generate a counting pulse signal, and send the counting pulse signal to a corresponding one of the counting units, wherein each of the window acquisition circuits comprises a plurality of acquisition modules, and the respective acquisition modules are connected in parallel with each other and configured to acquire the voltage pulse signals of different amplitudes;
   each of the acquisition modules comprising a high threshold voltage comparator and a low threshold voltage comparator that are connected in parallel;
   each of the counting units comprises a plurality of counting subunits, the counting subunits are connected in one-to-one correspondence to the acquisition modules; each of the counting subunits is configured to receive the counting pulse signal, count the counting pulse signal to obtain a counted value, and send the counted value to the processor;
   each of the counting subunits comprising two counters, with the high threshold voltage comparator and the low threshold voltage comparator connected in one-to-one correspondence to the two counters; and
   the processor is connected to each of the counting subunits, and the processor is configured to receive the counted value and generate, based on the counted value, an in vivo radioactive material distribution grayscale image.

2. The device according to claim 1, wherein the plurality of CZT detectors are arranged in a form of linear array.

3. The device according to claim 1, wherein each of the data processing units comprises an amplifier and an integrator, and the CZT detector, the amplifier, the integrator, and the window acquisition circuit are connected in sequence.

4. The device according to claim 3, wherein each of the data processing units further comprises a pulse shaping circuit, an input terminal of the pulse shaping circuit is connected to an output terminal of the integrator, and an output terminal of the pulse shaping circuit is connected to an input terminal of the window acquisition circuit.

5. The device according to claim 1, further comprising a collimator, wherein the collimator is provided with a plurality of channels, the respective channels are connected in one-to-one correspondence to the respective CZT detectors, and each of the channels is configured to capture the γ-ray such that the γ-ray is transmitted to the CZT detector.

6. The device according to claim 1, wherein the device further comprises a display, the display is connected to the processor and configured to receive and display the in vivo radioactive material distribution grayscale image.

7. The device according to claim 1, wherein the device further comprises a latch, and the latch is connected to the counters and the processor; and the latch is configured to latch the counted values sent from the counters, and transmit the counted values to the processor for processing.

8. A radiation residue scanning system, comprising a base, a support body, a height measuring device, a lifting device, and the radiation residue scanning device according to claim 1;
   wherein the base is connected to the support body and configured to bear a patient who is in a standing state, and the height measuring device is mounted on the support body and configured to measure a height of the patient;
   the height measuring device is connected to the processor, and the processor is further configured to receive the height, determine, based on the height, an initial scanning position and a final scanning position, and send a driving signal to the lifting device; and
   the lifting device is mounted on the support body and movable up and down, and the radiation residue scanning device is mounted in the lifting device; the lifting device is electrically connected to the processor; and the lifting device is configured to drive, based on the driving signal, the radiation residue scanning device to move up and down.

9. The system according to claim 8, wherein the system further comprises a speed sensor electrically connected to the processor; the speed sensor is mounted on the lifting device; and the speed sensor is configured to acquire a moving speed of the lifting device and send the moving speed to the processor.

10. The system according to claim 8, wherein the plurality of CZT detectors are arranged in a form of linear array.

11. The system according to claim 8, wherein each of the data processing units comprises an amplifier and an integrator, and the CZT detector, the amplifier, the integrator, and the window acquisition circuit are connected in sequence.

12. The system according to claim 8, wherein each of the acquisition modules comprises a high threshold voltage comparator and a low threshold voltage comparator that are connected in parallel; and each of the counting subunits comprises two counters, with the high threshold voltage comparator and the low threshold voltage comparator connected in one-to-one correspondence to the two counters.

13. The system according to claim 8, wherein each of the data processing units further comprises a pulse shaping circuit, an input terminal of the pulse shaping circuit is connected to an output terminal of the integrator, and an output terminal of the pulse shaping circuit is connected to an input terminal of the window acquisition circuit.

14. The system according to claim 8, wherein the device further comprises a collimator, wherein the collimator is provided with a plurality of channels, the respective channels are connected in one-to-one correspondence to the respective CZT detectors, and each of the channels is configured to capture the γ-ray such that the γ-ray is transmitted to the CZT detector.

15. The system according to claim 8, wherein the device further comprises a display, the display is connected to the processor and configured to receive and display the in vivo radioactive material distribution grayscale image.

16. The system according to claim 8, wherein the device further comprises a latch, and the latch is connected to the counters and the processor; and the latch is configured to latch the counted values sent from the counters, and transmit the counted values to the processor for processing.

* * * * *